United States Patent [19]

Hansen

[11] Patent Number: 5,276,028
[45] Date of Patent: Jan. 4, 1994

[54] IMIDAZOQUINOXALINE COMPOUNDS

[75] Inventor: Holger C. Hansen, V rlose, Denmark

[73] Assignee: Nordisk A/S, Bagsvaerd, Denmark

[21] Appl. No.: 949,311

[22] Filed: Sep. 22, 1992

Related U.S. Application Data

[62] Division of Ser. No. 712,324, Jun. 7, 1991, abandoned.

[30] Foreign Application Priority Data

Jun. 22, 1990 [DK] Denmark .............................. 1518/90

[51] Int. Cl.$^5$ ................ A61K 31/505; A61K 31/495; C07D 487/04
[52] U.S. Cl. ............................ 514/228.5; 514/233.2; 514/250; 544/60; 544/115; 544/250; 544/346
[58] Field of Search ............................ 514/250, 233.2; 544/346, 60, 115

[56] References Cited

U.S. PATENT DOCUMENTS

| | | | |
|---|---|---|---|
| 4,031,079 | 6/1977 | Mohrbacher et al. | 260/239.3 |
| 4,359,420 | 11/1982 | Gerecke et al. | 260/239.3 |
| 4,440,929 | 4/1984 | Lee | 544/346 |
| 4,771,051 | 9/1988 | Wätjen et al. | 514/267 |
| 4,774,245 | 9/1988 | Wätjen et al. | 514/250 |
| 4,873,244 | 10/1989 | Wätjen et al. | 514/250 |
| 5,075,304 | 12/1991 | Hansen | 544/346 |

FOREIGN PATENT DOCUMENTS

| | | |
|---|---|---|
| 0225013 | 6/1987 | European Pat. Off. . |
| 0226282 | 6/1987 | European Pat. Off. . |
| 0283162 | 9/1988 | European Pat. Off. . |
| 0320136 | 6/1989 | European Pat. Off. . |
| 0344943 | 12/1989 | European Pat. Off. . |
| 0347094 | 12/1989 | European Pat. Off. . |

OTHER PUBLICATIONS

Hansen, Chem. Abs. 76, 174168 (1991).

Primary Examiner—Mark L. Berch
Attorney, Agent, or Firm—Steve T. Zelson; Elias J. Lambiris

[57] ABSTRACT

The heterocyclic compounds having the general formula I

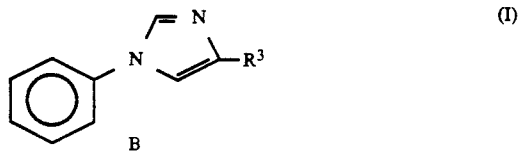

wherein
$R^3$ is

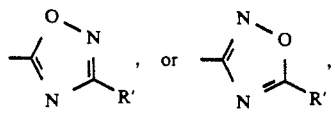

wherein R' is H, $C_{1-6}$-alkyl or $C_{3-7}$-cycloalkyl;
—B— is —C(R")=N— or —N=C(R")— wherein R" is a cyclic amine or —NR'"R"", wherein R'" and R"" independently are H, $C_{1-6}$-alkoxy, $C_{3-7}$-cycloalkyl or $C_{1-6}$-alkyl.

The compounds are useful in psychopharmaceutical preparations as anticonvulsants, anxiolytics, hypnotics and in improving the cognitive function of the brain of mammals.

7 Claims, No Drawings

IMIDAZOQUINOXALINE COMPOUNDS

This is a divisional application of co-pending application Ser. No. 07/712,324, filed Jun. 7, 1991, now abandoned.

The present invention relates to therapeutically active heterocyclic compounds, a method of preparing the same, pharmaceutical compositions comprising the compounds, and to methods of treating therewith. The novel compounds are useful in psychopharmaceutical applications, e.g., in the treatment of central nervous system ailments, for example, as anticonvulsants or anxiolytics, hypnotics, in treating emesis, schizophrenia, or in improving the cognitive function of the brain.

It is well known (Squires, R. F. and Braestrup, C. in Nature (London) 266 (1977) 732-734) that specific sites in the central nervous systems of vertebrates exhibit a high specific affinity for binding 1,4- and 1,5-benzodiazepines. These sites are called benzodiazepine receptors.

It has now been found that members of a novel group of aminoimidazoquinoxaline and -quinazoline compounds have strong affinity for the benzodiazepine receptors which make them useful in psychopharmaceutical preparations.

Accordingly, it is an object of the invention to provide such novel 4-aminoimidazoquinoxaline and 5-aminoimidazoquinazoline compounds.

The compounds of the invention have the general formula I

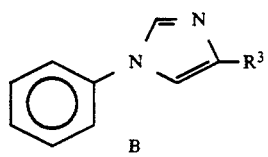

wherein
$R^3$ is

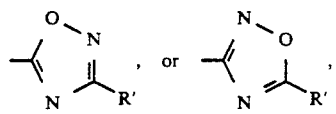

wherein R' is H, $C_{1-6}$-alkyl or $C_{3-7}$-cycloalkyl;
—B— is —C(R")=N— or —N=C(R")— wherein R" is a cyclic amine or —NR'''R'''', wherein R''' and R'''' independently are H, $C_{1-6}$-alkoxy, $C_{3-7}$-cycloalkyl or $C_{1-6}$-alkyl.

The invention also relates to a method of preparing the above mentioned compounds. This method comprises:

a) reacting a compound of formula II

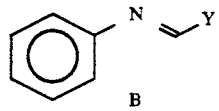

wherein —B— has the meaning set forth above and wherein Y is a leaving group, with a compound having the formula III

wherein $R^3$ has the meaning set forth above, to form a compound of the invention, or b) reacting a reactive derivative of a compound having the general formula IV

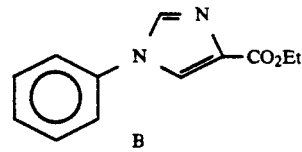

wherein —B— has the meaning set forth above, with a compound having the general formula V

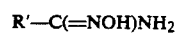

wherein R' has the meaning set forth above to form a compound of the general formula I wherein $R^3$ is

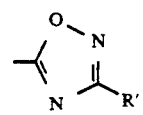

wherein R' has the meaning set forth above, or c) reacting a compound having the general formula VI

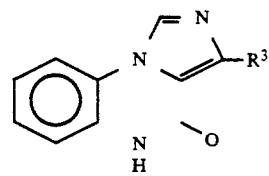

wherein $R^3$ has the meaning set forth above, with POCl₃ to form a compound of formula VII

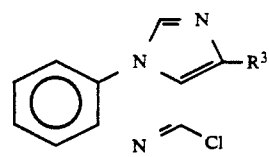

which is reacted with a compound of formula VIII

to form a compound of the general formula I wherein B is

wherein R" is —NR'''R'''', wherein R''' and R'''' have the meanings set forth above.

The leaving group, Y, may be any suitable leaving group and, for example, those disclosed in U.S. Pat. Nos. 4,031,079 or 4,359,420, for example, halogen, alkylthio, e.g., methylthio, aralkylthio, N-nitrosoalkylamino, alkoxy, mercapto, —OP(O)(OR)₂ wherein R is lower-alkyl or —OP(O)(NR'R")₂ wherein R' and R"

each represents lower-alkyl or phenyl, or together with the nitrogen atom to which they are attached represent a heterocyclic radical such as morpholino, pyrrolidino, piperidino, or methylpiperazino. The reaction is preferably carried out under alkaline conditions, i.e., in the presence of a base, and among bases alkali metal, e.g., potassium or sodium, alkoxides or hydrides are preferred. The reaction is preferably conducted in the presence of an organic solvent which is nonreactive with the reactants and products of reaction under the conditions of reaction, especially an anhydrous solvent and preferably an anhydrous aprotic solvent such as dimethylformamide (DMF) or the like. The temperature range employed may be any range suitable for the reaction to proceed at a reasonable rate and without undue delay or decomposition and a range from a minus forty ($-40$) degrees Celsius to about room temperature is accordingly usually particularly suitable.

The starting materials may be prepared from commercially available organic compounds and by using well known synthetic methods.

The pharmaceutical properties of the compounds of the invention can be illustrated by determining their capability for displacing radioactive labelled flunitrazepam from benzodiazepine receptors.

The displacement activity of the compounds of the invention may be found by determining the $ED_{50}$ value. The $ED_{50}$ value represents the dose (mg/kg) of a test substance which causes the specific binding of flunitrazepam to benzodiazepine receptors in a living brain to be reduced to 50% of the control value.

Such an in vivo test is carried out as described in U.S. Pat. No. 4,774,245.

Test results obtained by testing some compounds of the invention will appear from the following table I.

TABLE 1

| Compound | $ED_{50}$ (mg/kg) |
|---|---|
| 4 | 4.1 |
| 19 | 1.6 |
| 14 | 1.9 |
| 13 | 1.5 |

The compound of the invention, together with a conventional adjuvant, carrier, or diluent, and if desired in the form of a pharmaceutically-acceptable acid addition salt thereof, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective central nervous system ailment alleviating amount of the active ingredient commensurate with the intended daily dosage range to be employed. Tablets containing one (1) milligram of active ingredient or, more broadly, one (1) to thirty (30) milligrams, per tablet, are accordingly suitable representative unit dosage forms.

The compounds of this invention can thus be used for the formulation of pharmaceutical preparations, e.g., for oral and parenteral administration to mammals including humans, in accordance with conventional methods of galenic pharmacy.

Conventional excipients are such pharmaceutically acceptable organic or inorganic carrier substances suitable for parenteral or oral application which do not deleteriously react with the active compound.

Examples of such carriers are water, salt solutions, alcohols, polyethylene glycols, polyhydroxyethoxylated castor oil, gelatin, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxilliary agents, such as lubricants, preservatives, stabilizers, wetting agents, emulsifiers, salt for influencing osmotic pressure, buffers and/or coloring substances and the like, which do not deleteriously react with the active compound.

For parenteral application, particularly suitable are injectable solutions or suspensions, preferably aqueous solutions with the active compound dissolved in polyhydroxylated castor oil.

Ampoules are convenient unit dosage forms.

For oral application, particularly suitable are tablets, dragees, or capsules having talc and/or a carbohydrate carrier or binder or the like, the carrier preferably being lactose and/or corn starch and/or potato starch. A syrup, elixir or like can be used when a sweetened vehicle can be employed. Generally, as to broader ranges, the compounds of the invention are dispensed in unit dosage form comprising 0.05-100 mg in a pharmaceutically-acceptable carrier per unit dosage.

A typical tablet which may be prepared by conventional tabletting techniques contains:

| | |
|---|---|
| Active compound | 1.0 mg |
| Lactosum | 67.8 mg Ph. Eur. |
| Avicel ® | 31.4 mg |
| Amberlite ® IRP 88 | 1.0 mg |
| *Magnesii stearas* | 0.25 mg Ph. Eur. |

Due to their high degree of affinity for the benzodiazepin receptors, the compounds of the invention are extremely useful in the treatment of central nervous system ailments or disorders, when administered in an amount effective for the alleviation, amelioration, or elimination thereof. The important CNS activity of the compounds of the invention includes both anticonvulsant and anxiolytic activities along with a low toxicity, together presenting a most favorable therapeutic index. The compounds of the invention may accordingly be administered to a subject, e.g., a living animal or a human body, in need of the same for the treatment, alleviation, amelioration, or elimination of an indication, associated with the central nervous system and the so-called benzodiazepine receptors, which requires such psychopharmaceutical treatment, e.g., especially convulsion, insomnia, dementia and/or anxiety states, if desired in the form of a pharmaceutically acceptable acid addition salt thereof (such as the hydrobromide, hydrochloride, or sulfate, in any event prepared in the usual or conventional manner, e.g., evaporation to dryness of the free base in solution together with the acid), ordinarily concurrently, simultaneously, or together with a pharmaceutically-acceptable carrier or diluent, especially and preferably in the form of a pharmaceutical composition thereof, whether by oral, rectal, or parenteral (including subcutaneous) route, in an effective psychopharmaceutical central nervous system ailment alleviating amount, e.g., an anticonvulsant and/or anxiolytic amount, and in any event an amount which is effective for the alleviation of such a central nervous system ailment due to their benzodiazepine receptor affinity. Suitable dosage ranges are 1-200 milligrams daily, 1-100 milligrams daily, and especially 1-30 milligrams daily, depending as usual upon the exact mode of administration, form in which administered, the indication toward which the administration is directed, the subject involved and the body weight of the subject involved, and the preference and experience of the physician or veterinarian in charge.

The invention will now be described in further detail with reference to the following examples:

EXAMPLE 1

4-chloro-3-(5-cyclopropyl-1,2,4-oxadiazol-3-yl)-imidazo-[1,5-a]quinoxaline

A ground mixture of 3-(5-cyclopropyl-1,2,4-oxadiazol-3-yl)-4,5-dihydro-4-oxo-imidazo[1,5-a]quinoxaline (3.76 g, 13 mmol) and phosphorus pentachloride (2.67 g, 13 mmol) in phosphorus oxychloride (10 ml) was stirred for 2 h at 150°-160° C. The resulting solution while still warm was poured into 200 ml of ice and stirred for 1 h. The precipitate was collected by filtration, rinsed with water and dried to give 3.4 g of the title compound, m.p. 140°-150° C. (dec.). The crude product obtained in this way was processed without further purification. (Compound 1).

Similarly, 4-chloro-3-(3-cyclopropyl-1,2,4-oxadiazol-5-yl)imidazo[1,5-a]quinoxaline, m.p. 166°-168° C. was prepared from 3-(3-cyclopropyl-1,2,4-oxadiazol-5-yl)-4,5-dihydro-4-oxoimidazo[1,5-a]quinoxaline. (Compound 2).

EXAMPLE 2

4-Amino-3-(5-cyclopropyl-1,2,4-oxadiazol-3-yl)-imidazo-[1,5-a]quinoxaline

A stirred solution of 4-chloro-3-(5-cyclopropyl-1,2,4-oxadiazol-3-yl)-imidazo[1,5-a]quinoxaline (0.15 g) in 10 ml of a 1:1 mixture of $CH_2Cl_2$ and ethanol was saturated with ammonia. The reaction was monitored by t.l.c. (silica gel/$CH_2Cl_2$-acetone 4:1) and ammonia was bubbled through the solution in between. When the reaction was completed, the solvent was evaporated in vacuo and the residue was triturated with 10 ml of water. The precipitate was filtered off, rinsed with water and dried to give 0.12 g of the title compound as white needles, m.p. 305°-310° C. (Compound 3).

EXAMPLE 3

3-(5-cyclopropyl-1,2,4-oxadiazol-3-yl)-4-dimethylaminoimidazo[1,5-a]quinoxaline hydrochloride Dimethylamine was bubbled through a solution of 4-chloro-3-(5-cyclopropyl-1,2,4-oxadiazol-3-yl)-imidazo[1,5-a]-quinoxaline (3.4 g) in dry THF (75 ml) for 5 min. whereafter the mixture was stirred for ½ h. The solvent was evaporated in vacuo and the residue was partioned between $CH_2Cl_2$ (60 ml) and 1M NaOH (30 ml). The organic layer was washed with water (30 ml) and then shaken with 4M HCl (60 ml). Pale crystals precipitated and were filtered off and dried to give 2.8 g of the title compound as a dihydrate, m.p. 216°-218° C. (Compound 4).

EXAMPLE 4

3-(3-cyclopropyl-1,2,4-oxadiazol-5-yl)-4-dimethylaminoimidazo[1,5-a]quinoxaline

Dimethylamine was bubbled through a solution of 4-chloro-3-(3-cyclopropyl-1,2,4-oxadiazol-5-yl)-imidazo[1,5-a]quinoxaline (1,5 g) in dry THF for 5 min. After stirring for ½ h the solvent was evaporated. The residue was purified by column chromatography (silica gel/ ethyl acetate - benzin 1:1) and the title compound was obtained as pale crystals, yield 0.4 g, m.p. 137°-140° C. (Compound 5).

Similarly, from 4-chloro-3-(3-cyclopropyl-1,2,4-oxadiazol-5-yl)-imidazo[1,5-a]quinoxaline and the appropriate amines in THF/triethylamine (10:1) the following compounds were prepared:

3-(3-cyclopropyl-1,2,4-oxadiazol-5-yl)-4-(N-ethyl-N-methylamino)-imidazo[1,5-a]quinoxaline, m.p. 113°-115° C. (Compound 6).

(3-cyclopropyl-1,2,4-oxadiazol-5-yl)-4-(N-methoxy-N-methylamino)-imidazo[1,5-a]quinoxaline, m.p. 142°-144° C. (Compound 7).

3-(3-cyclopropyl-1,2,4-oxadiazol-5-yl)-4-methylaminoimidazo-[1,5-a]quinoxaline, m.p. 262°-264° C. (Compound 8).

EXAMPLE 5

3-(5-cyclopropyl-1,2,4-oxadiazol-3-yl)-4-morpholinoimidazo[1,5-a]quinoxaline

A solution of potassium t-butoxide (3.7 g, 32 mmol) in dry DMF (25 ml) was added to a stirred solution of 2-chloro-3-morpholino-quinoxaline (4 g, 16 mmol) and 5-cyclopropyl-3-isocyanomethyl-1,2,4-oxadiazole in dry DMF (50 ml), the temperature being kept at 0°-5° C. Then the temperature was raised to 20° C. and the solvent was evaporated in vacuo. The residue was partitioned between water (50 ml) and dichloromethane (50 ml). The organic phase was dried and evaporated and the residue was triturated with a small amount of ethyl acetate. The resulting crystalline product was collected by filtration and dried to give 3.2 g of the title compound, m.p. 169°-173° C. (Compound 9).

In similar ways the following compounds were prepared:

3-(5-cyclopropyl-1,2,4-oxadiazol-3-yl)-4-(N-ethyl-N-methylamino)-imidazo[1,5-a]quinoxaline hydrochloride, from 2-chloro-3-(N-ethyl-N-methylamino)-quinoxaline and 5-cyclopropyl-3-isocyanomethyl-1,2,4-oxadiazole. The primary product, i.e. the free amine, was obtained as an oil. The hydrochloride, was prepared by dissolving the amine (0.20 g) in dry acetone (10 ml) and adding excess HCl in ether. The resulting precipitate was collected by filtration and dried to give the title compound, m.p. 200°-202° C. (Compound 10).

Ethyl 4-(N-ethyl-N-methylamino)-imidazo[1,5-a]quinoxaline-3-carboxylate, m.p. 108°-110° C., from 2-chloro-3-(N-ethyl-N-methylamino)-quinoxaline and ethyl isocyanoacetate. (Compound 11).

EXAMPLE 6

3-(3-cyclopropyl-1,2,4-oxadiazol-5-yl)-4-(N-ethyl-N-methylamino)-imidazo[1,5-a]quinoxaline A mixture of ethyl 4-(N-ethyl-N-methylamino)-imidazo[1,5-a]quinoxaline-3-carboxylate (1.2 g, 4 mmol), cyclopropanecarboxamidoxime (1.4 g, 14 mmol), crushed 4 Å molecular-sieves (0.5 g), and sodium hydride (0.1 g, 60% in mineral oil) in dry DMF (20 ml) was stirred at ambient temperature for 1 h. Dichloromethane (25 ml) was added and the mixture was filtered through celite. The filtrate was evaporated and the residue was brought to crystallize by the addition of 10 ml of ethyl acetate and cooling to 0° C. The crystals was collected by filtration, rinsed with ethyl acetate and dried to give 0.58 g of the title compound, m.p. 96°-97° C. An additional amount (0.22 g) of the product was obtained from the mother liquour. (Compound 6).

EXAMPLE 7

Ethyl 5-morpholino-imidazo[1,5-a]quinazoline-3-carboxylate

A solution of potassium t-butoxide (2.1 g, 19 mmol) in dry DMF (15 ml) was added during 15 min at 0°-5° C. to a stirred solution of 2-chloro-4-morpholino-quinazoline (3.0 g, 12 mmol) and ethyl isocyanoacetate (2.1 g, 19 mmol) in dry DMF (40 ml). The mixture was stirred at room temperature for 2 h. Then glacial acetic acid (2 ml) was added and the solvent was evaporated in vacuo.

The residue was triturated with a mixture of water (50 ml) and ethyl acetate (10 ml) giving the title compound as a pale yellow precipitate. The product was collected by filtration and rinsed with water and ethyl acetate and dried. Yield 3.6 g (91%), m.p. approx. 165° C., resolidifies to give crystals melting at 195.5°-196.5° C. (Compound 12).

In a similar manner the following compounds were prepared:

3-(5-cyclopropyl-1,2,4-oxadiazol-3-yl)-5-dimethylamino-imidazo[1,5-a]quinazoline, m.p. 175°-176° C., from 2-chloro-4-dimethylamino-quinazoline and 5-cyclopropyl-3-isocyanomethyl-1,2,4-oxadiazole. (Compound 13).

3-(5-cyclopropyl-1,2,4-oxadiazol-3-yl)-5-morpholino-imidazo[1,5-a]quinazoline, m.p. 203°-205° C., from 2-chloro-4-morpholino-quinazoline and 5-cyclopropyl-3-isocyanomethyl-1,2,4-oxadiazole. (Compound 14).

3-(5-cyclopropyl-1,2,4-oxadiazol-3-yl)-5-N-ethyl-N-methylamino)-imidazo[1,5-a]quinazoline, m.p. 161°-162° C. from 2-chloro-4-(N-ethyl-N-methylamino)-quinazoline and 5-cyclopropyl-3-isocyanomethyl-1,2,4-oxadiazole. (Compound 15).

Ethyl 6-chloro-5-morpholino-imidazo[1,5-a]quinazoline-3-carboxylate, m.p. 189°-191° C., from 2,5-dichloro-4-morpholino-quinazoline and ethyl isocyanoacetate. (Compound 16).

3-(5-cyclopropyl-1,2,4-oxadiazol-3-yl)-5-thiomorpholinoimidazo[1,5-a]quinazoline, m.p. 193°-196° C., from 2-chloro-4-thiomorpholino-quinazoline and 5-cyclopropyl-3-isocyanomethyl-1,2,4-oxadiazole. (Compound 17).

3-(3-cyclopropyl-1,2,4-oxadiazol-5-yl)-5-thiomorpholino-imidazo[1,5-a]quinazoline, m.p. 228°-233° C., from 2-chloro-4-thiomorpholino-quinazoline and 3-cyclopropyl-5-isocyanomethyl-1,2,4-oxadiazole. (Compound 18).

EXAMPLE 8

3-(3-cyclopropyl-1,2,4-oxadiazol-5-yl)-5-morpholino-imidazo[1,5-a]quinazoline A mixture of ethyl 5-morpholino-imidazo[1,5-a]quinazoline-3-carboxylate (2.5 g, 7.7 mmol), cyclopropanecarboxamide oxime (3.8 g), crushed 4 Å molecular sieves (7.5 g), and sodium hydride (0.3 g, 60% in mineral oil, 7.7 mmol) in 50 ml of dry DMF was stirred at room temperature for 1 h. Glacial acetic acid (2 ml) and dichloromethane (75 ml) was added, and the mixture was filtered through celite. The filtrate was evaporated and the residue was triturated with water (100 ml). Pale yellow crystals precipitated and was collected by filtration and dried to give 2.3 g of the title compound, m.p. 189°-191° C. A pure product was obtained by recrystallization from $CH_2Cl_2$/ethyl acetate; yield 1.9 g (69%), m.p. 197°-198° C. (Compound 19).

In the same way the following compound was prepared:

6-chloro-3-(3-cyclopropyl-1,2,4-oxadiazol-5-yl)-5-morpholino-imidazo[1,5-a]quinazoline, m.p. 245°-246° C., from ethyl 6-chloro-5-morpholino-imidazo[1,5-a]quinazoline-3-carboxylate and cyclopropanecarboxamide oxime. (Compound 20)

I claim:

1. A compound of formula I:

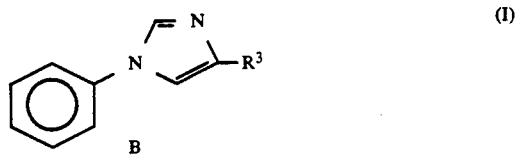

wherein
$R^3$ is

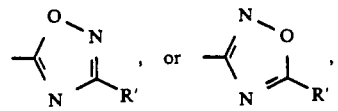

wherein R' is H, $C_{1-6}$-alkyl or $C_{3-7}$-cycloalkyl;
—B— is —N=C(R")— wherein R" is morpholino, thiomorpholino or —NR'''R'''', wherein R''' and R'''' independently are H, $C_{1-6}$-alkoxy, $C_{3-7}$-cycloalkyl or $C_{1-6}$-alkyl; or a pharmaceutically acceptable salt thereof.

2. A compound which is 3-(5-cyclopropyl-1,2,4-oxadiazol-3-yl)-4-dimethylamino-imidazo[1,5-a]quinoxaline.

3. A pharmaceutical composition comprising a compound according to claim 1 together with a pharmaceutically-acceptable carrier or diluent.

4. A pharmaceutical composition according to claim 3 in the form of an oral dosage unit containing 1-100 mg of the compound.

5. A method for treating convulsions, anxiety or for exerting a hypnotic effect in a subject in need thereof comprising administering an effective amount of a compound according to claim 1.

6. A method for treating convulsions, anxiety or for exerting a hypnotic effect in a subject in need thereof comprising administering a pharmaceutical composition according to claim 3.

7. A compound which is 4-amino-3-(5-cyclopropyl-1,2,4-oxadiazol-3-yl)-imidazo[1,5-a]quinoxaline.

* * * * *

UNITED STATES PATENT AND TRADEMARK OFFICE
CERTIFICATE OF CORRECTION

PATENT NO. : 5,276,028
DATED : January 4, 1994
INVENTOR(S) : Holger Claus Hansen It is certified that error appears in the above-indentified patent and that said Letters Patent is hereby corrected as shown below:

Title page, Item [73]: after "Assignee:" insert -- Novo --.

Signed and Sealed this

Tenth Day of October, 1995

*Attest:*

BRUCE LEHMAN

*Attesting Officer*   Commissioner of Patents and Trademarks